(12) United States Patent
Carlson

(10) Patent No.: US 8,905,923 B2
(45) Date of Patent: Dec. 9, 2014

(54) SURGICAL RETRACTOR FOR WRIST PROCEDURES

(71) Applicant: Dextimus, LLC, Incline Village, NV (US)

(72) Inventor: Michelle G. Carlson, New York, NY (US)

(73) Assignee: Dextimus, LLC, Incline Village, NV (US)

( * ) Notice: Subject to any disclaimer, the term of this patent is extended or adjusted under 35 U.S.C. 154(b) by 274 days.

(21) Appl. No.: 13/668,524

(22) Filed: Nov. 5, 2012

(65) Prior Publication Data

US 2014/0128684 A1    May 8, 2014

(51) Int. Cl.
*A61B 1/32* (2006.01)

(52) U.S. Cl.
USPC .......................................................... 600/217

(58) Field of Classification Search
CPC ....................................................... A61B 17/02
USPC .......................................................... 600/217
See application file for complete search history.

(56) References Cited

U.S. PATENT DOCUMENTS

| | | | |
|---|---|---|---|
| 3,651,800 A * | 3/1972 | Wilbanks | 600/210 |
| 5,303,694 A | 4/1994 | Mikhail | |
| 5,334,194 A | 8/1994 | Mikhail | |
| 5,351,680 A | 10/1994 | Jung | |
| 5,846,192 A | 12/1998 | Teixido | |
| 5,906,210 A | 5/1999 | Herbert | |
| 6,663,562 B2 | 12/2003 | Chang | |
| 7,108,698 B2 | 9/2006 | Robbins et al. | |
| 7,214,186 B2 | 5/2007 | Ritland | |
| D549,331 S | 8/2007 | Tomatsu | |
| 2007/0060795 A1 * | 3/2007 | Vayser et al. | 600/245 |
| 2007/0066872 A1 | 3/2007 | Morrison et al. | |
| 2007/0093696 A1 | 4/2007 | Sharratt | |
| 2009/0149716 A1 | 6/2009 | Diao et al. | |
| 2009/0281578 A1 | 11/2009 | Spencer | |
| 2011/0054262 A1 | 3/2011 | Cobb et al. | |
| 2011/0137128 A1 | 6/2011 | Poo et al. | |

FOREIGN PATENT DOCUMENTS

WO    WO2010086015    8/2010

OTHER PUBLICATIONS

Innomed, Modified Hohmann Retractors, 2011, Savannah, Georgia, 1 page.
Stryker Corporation, Reduction Instruments, 2009, Literature No. 982346, Switzerland, 16 pages.
Smith & Nephew, Hohmann Retractors, Catalog, 2012, 3 pages.

* cited by examiner

*Primary Examiner* — Sameh Boles
(74) *Attorney, Agent, or Firm* — Larry K. Roberts

(57) ABSTRACT

A surgical retractor configured for use in surgical procedures to repair patient wrist distal radius bone fractures. The retractor includes an elongated handle portion, a wing portion coupled to the handle portion, and a hook portion at a working end of the retractor. The hook portion is configured to engage the radius bone of a surgical patient during a procedure. The wing portion is positioned intermediate the hook portion and the elongated handle portion and configured with a sufficient width to retract the patient's pronator quadratus muscle, while having a height such that the wing portion does not contact the median nerve of the surgical patient. A portion of the retractor above the wing portion is configured to contact the median nerve while being sufficiently narrow so as not put excessive pressure on the median nerve to cause nerve damage.

7 Claims, 7 Drawing Sheets

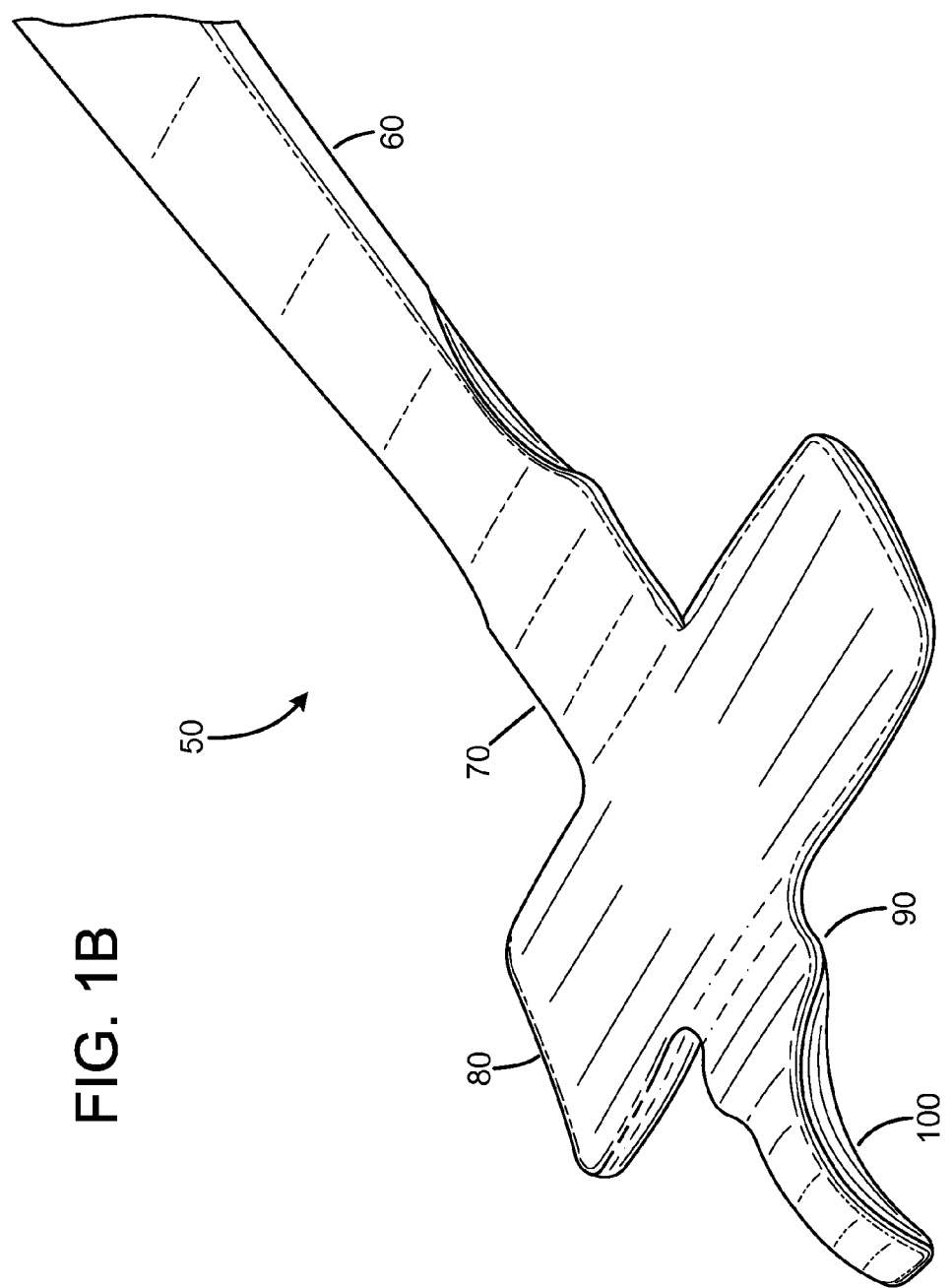

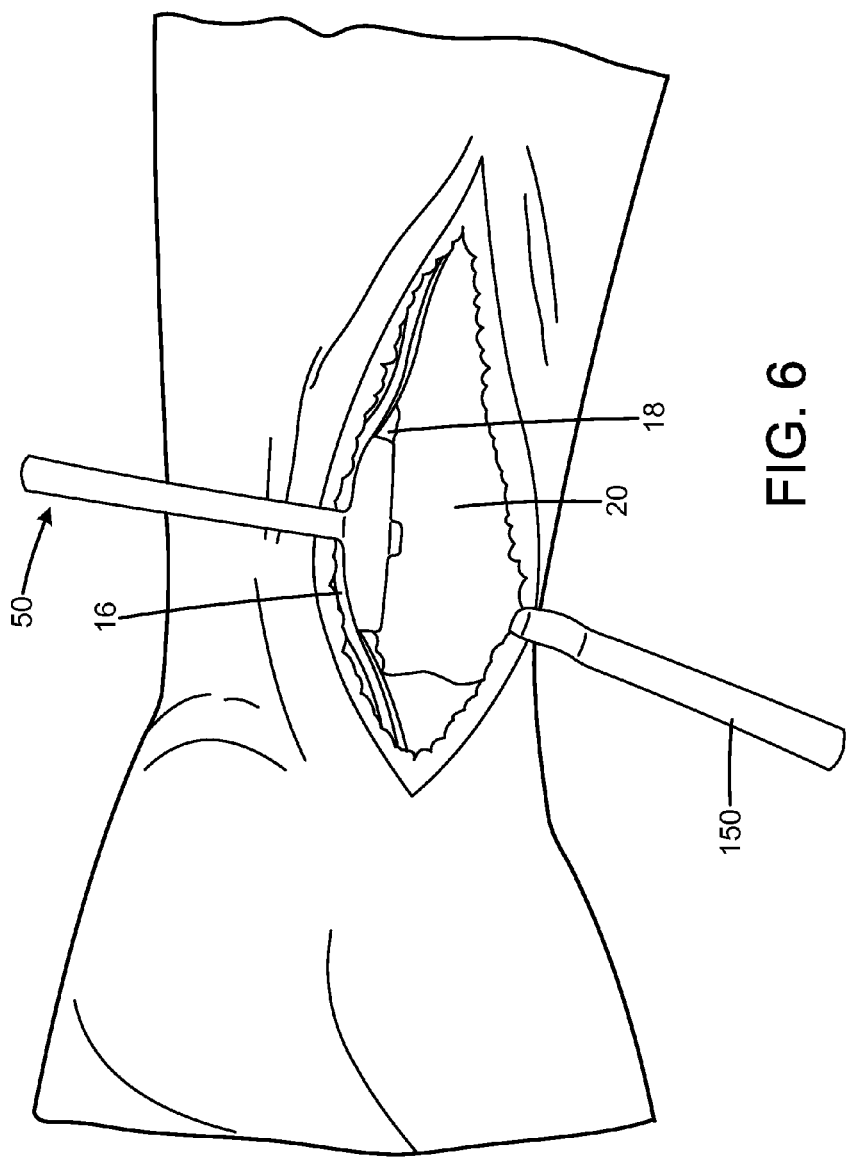

SURGICAL RETRACTOR FOR WRIST PROCEDURES

BACKGROUND

It is estimated that there are 400,000 wrist (distal radius) fractures per year in the United States. Among patients of Medicare age, up to 40% of these are treated operatively. In younger patients the numbers may be even higher.

Over the past ten years there has been a revolution in the approach to distal radius fractures. With the advent of the new locked volar plates, there has been a significant increase in the use of the volar approach to the distal radius, and in fact for many surgeons this is the only treatment. This approach involves retracting the deep pronator quadratus muscle from the distal radius, while not stretching the overlying median nerve, to expose the bone and facilitate plate application

BRIEF DESCRIPTION OF THE DRAWINGS

Features and advantages of the disclosure will readily be appreciated by persons skilled in the art from the following detailed description when read in conjunction with the drawing wherein:

FIG. 1B is an isometric view of the surgical retractor of FIG. 1A, taken from a reverse angle.

FIG. 6 is a diagrammatic view similar to FIG. 5, showing the use of the retractor from a different viewing angle.

DETAILED DESCRIPTION

Figure 1A:
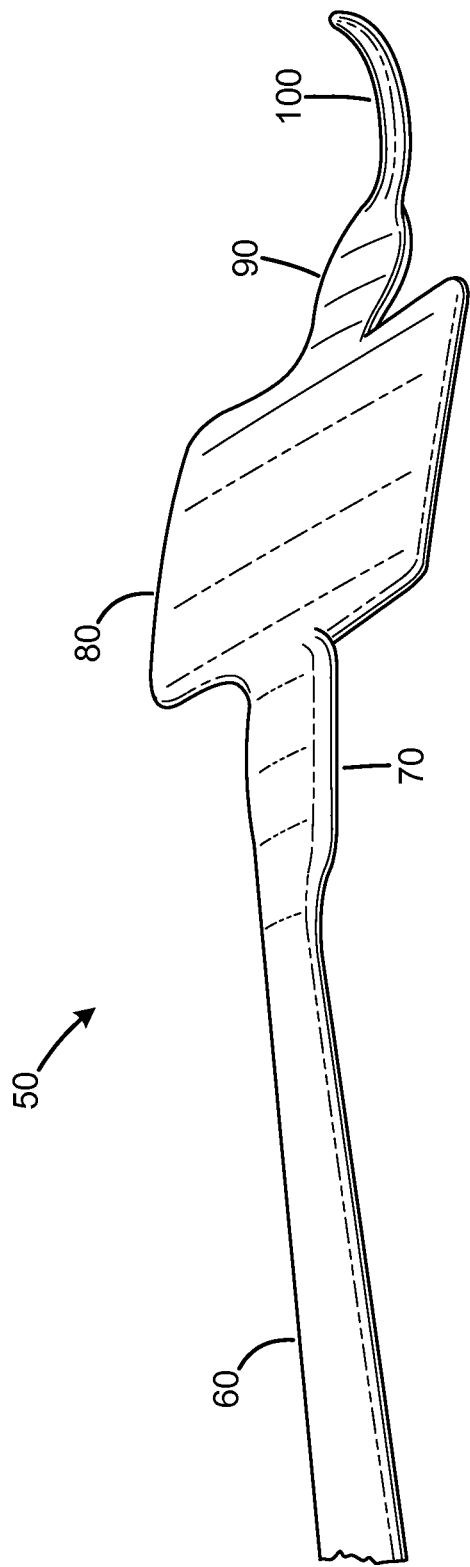
FIG. 1A is an isometric view of a portion of an exemplary embodiment of a surgical retractor.

In the following detailed description and in the several figures of the drawing, like elements are identified with like reference numerals. The figures may not be to scale, and relative feature sizes may be exaggerated for illustrative purposes.

The conventional retractors that hook on the bone and retract soft tissue (such as the Hohmann retractor) are narrow and ill-suited to keep the entire pronator muscle retracted while applying a volar plate to the fractured distal wrist bone. With these retractors it is a struggle keeping the pronator muscle out of the way so that the plate and screws can be applied. Because a Hohman retractor is too narrow to sufficiently retract the pronator, a second retractor is often necessary. Holding two retractors is cumbersome. If, instead of two retractors, a uniformly wider retractor were to be used to retract the pronator muscle fully, it puts too much pressure superficially on the overlying median nerve potentially causing nerve damage.

Exemplary embodiments of a pronator retractor according to aspects of the present invention are configured to hook on the radius bone, be wide at its lower portion or base to retract the pronator, and narrow at its upper portion or top region so as to not put too much pressure on the more superficial median nerve, and so may address the problems referred to above.

FIGS. 1A-5 illustrate an exemplary embodiment of a surgical retractor 50 configured for surgical use in repair of distal radius fractures. The retractor 50 includes a handle portion 60, a first intermediate portion 70, a wing or flange portion 80, a second intermediate portion 90, and a hook portion 100 at a distal end from the handle portion 60. The intermediate portions 70 and 90 have a somewhat wider profile than the handle portion 60, yet are much narrower than the wing portion 80. The intermediate portion 70 is sized and positioned to provide slight retraction on the soft tissue (tendons and nerve) above the pronator. The intermediate portion 90 serves to stabilize the retractor on the radius bone, and provides a greater surface area to contact the bone as the tip is hooked under the bone.

The handle portion 60 is of a length to provide the user with a grasping length, and to provide some leverage in applying pressure to retract the soft tissue away from the bone, to provide an open unobstructed field for the surgeon in a wrist incision.

The transverse wing portion 80 is sized to be positioned against the pronator muscle with the tip 100 hooked on or engaged against the radius bone, with a sufficient width to retract the pronator muscle away from the field of interest, while having a low enough height that the wing portion does not significantly engage the median nerve. The intermediate portion 70 of the retractor, just above the wing portion, is positioned against the median nerve, and with its width reduced in comparison to the wing portion, can apply retraction force over a reduced area, thus reducing the possibility of nerve damage. In another embodiment, the intermediate portions 70 and/or 90 may have the same or similar width as the handle portion 60; however, using the wider dimensions of these portions 70 and 90 provides improved retraction and stabilization.

An exemplary embodiment of the pronator retractor 50 has a transverse wing portion approximately 1.4 cm from the bottom tip of the retractor. The wing portion has overall dimensions of 2.5 cm in width by 1.2 cm in height. When the tip of the retractor is hooked around the radius, this wing portion will be positioned to retract the entire pronator muscle and will keep the field clear for the surgeon. The more superficial aspect of the retractor at portion 70 is narrower than the wing portion 80. The exemplary embodiment can have the following dimensions, and the following ranges of dimensions, with reference to FIG. 3:

D1=1.2 cm, within a range of 0.75 to 1.75 cm.
D2=2.5 cm, within a range of 2. to 3.5 cm.
D3=1.4 cm, within a range of 0.8 to 2. cm.
D4=0.8 cm, within a range of 0.4 to 1.2 cm.
D5=0.6 cm, within a range of 0.4 to 0.8 cm.
D6=0.8 cm, within a range of 0.4 to 1.2 cm.
D7=0.3 cm, within a range of 0.2 to 0.5 cm.

Figure 2:
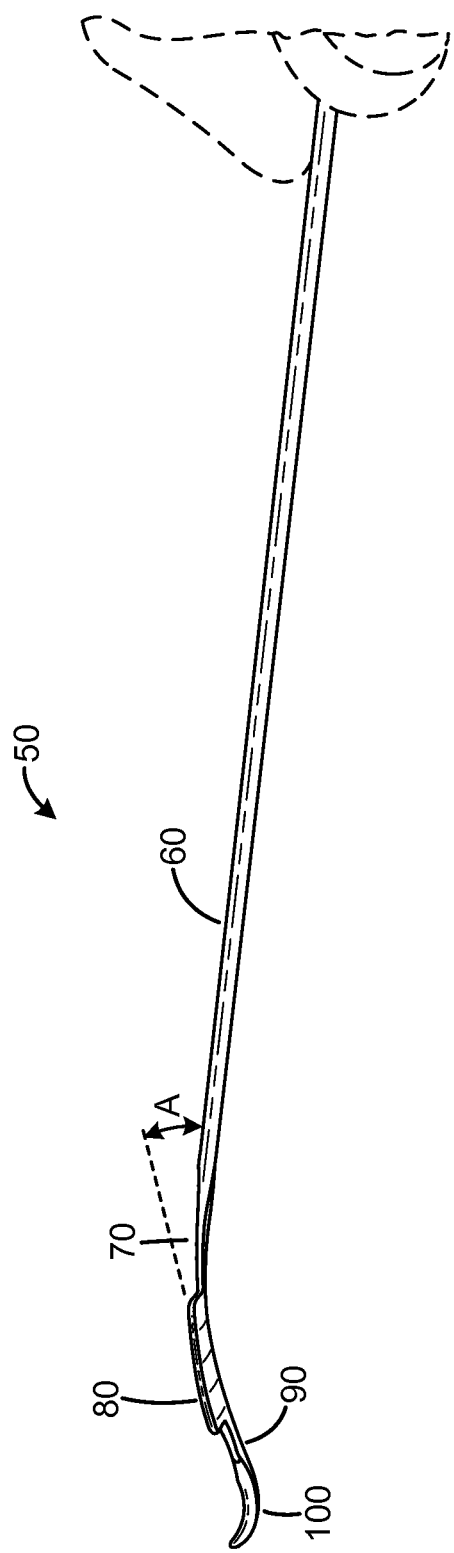
FIG. 2 is a side view of the surgical retractor of FIG. 1A.
Figure 3:
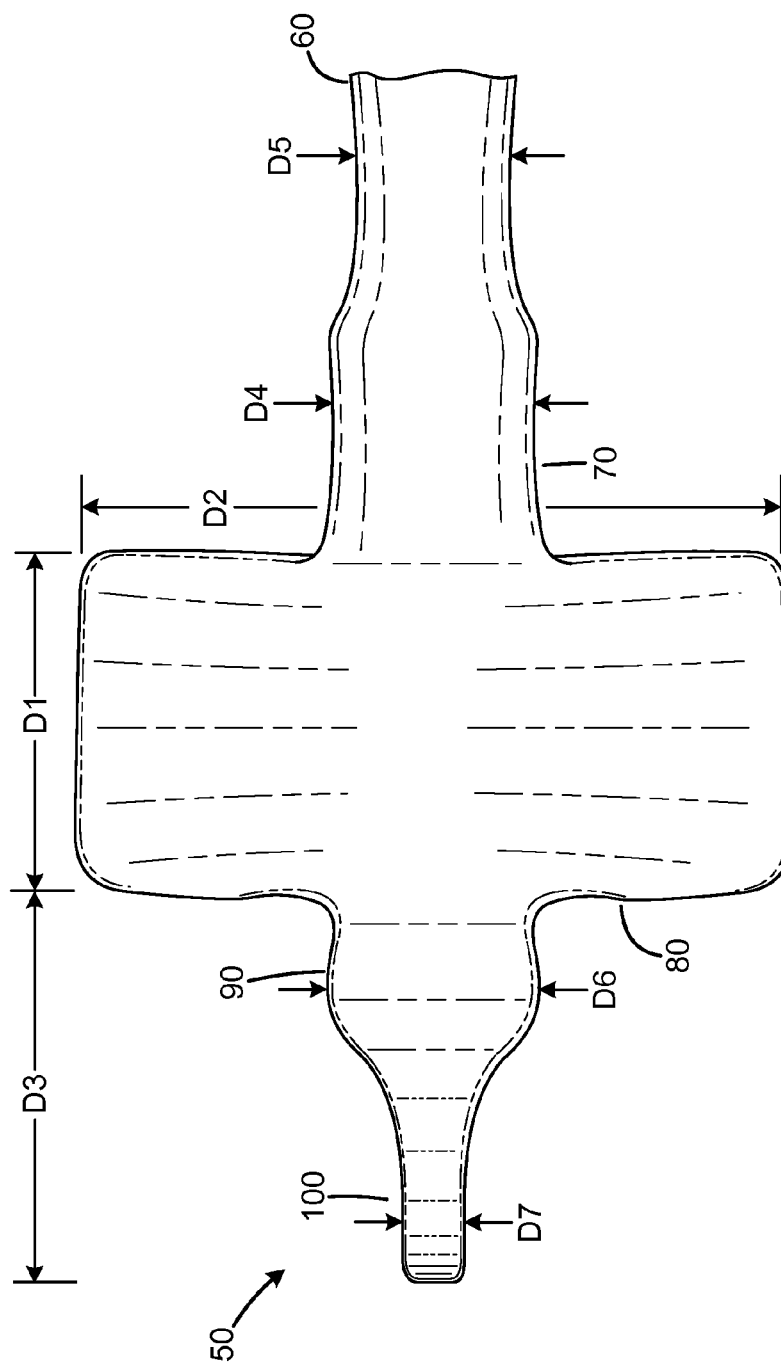
FIG. 3 is a top view of the surgical retractor of FIG. 1A.
Figure 4:
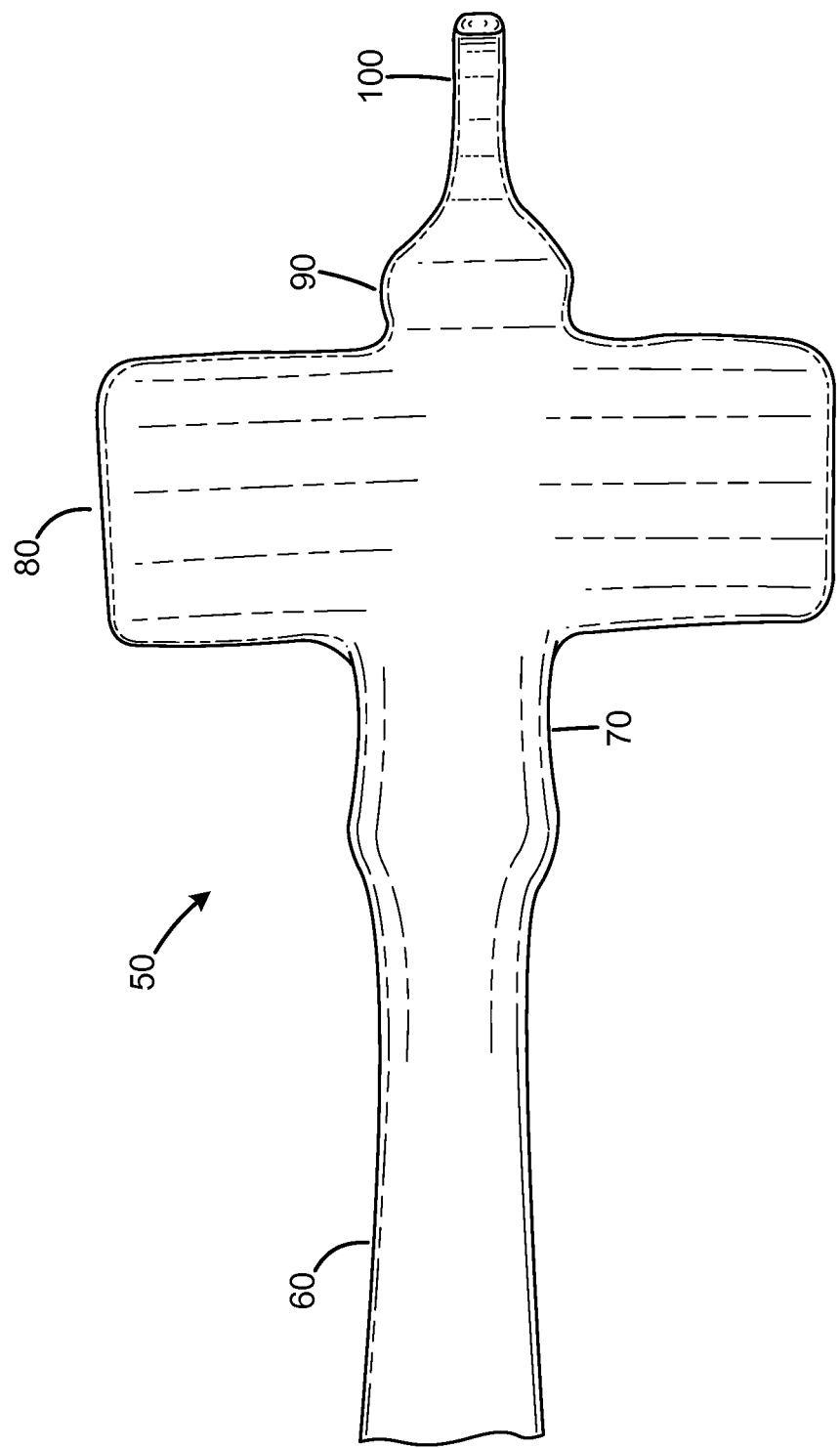
FIG. 4 is a bottom view of the surgical retractor of FIG. 1A.

Referring to the side view of FIG. 2, in an exemplary embodiment, the portions 80, 90 are bent or disposed at an angle A relative to the handle portion 60. An exemplary suitable range of the angle A is between 10 degrees and 40 degrees. The angular orientation of the portions 80, 90 of the retractor relative to the handle serves to position the handle portion 60 further away from the field of interest within the patient's wrist. The thickness of the retractor will depend on the material from which it is made; an exemplary suitable range is between 1 mm and 4 mm.

Figure 5:
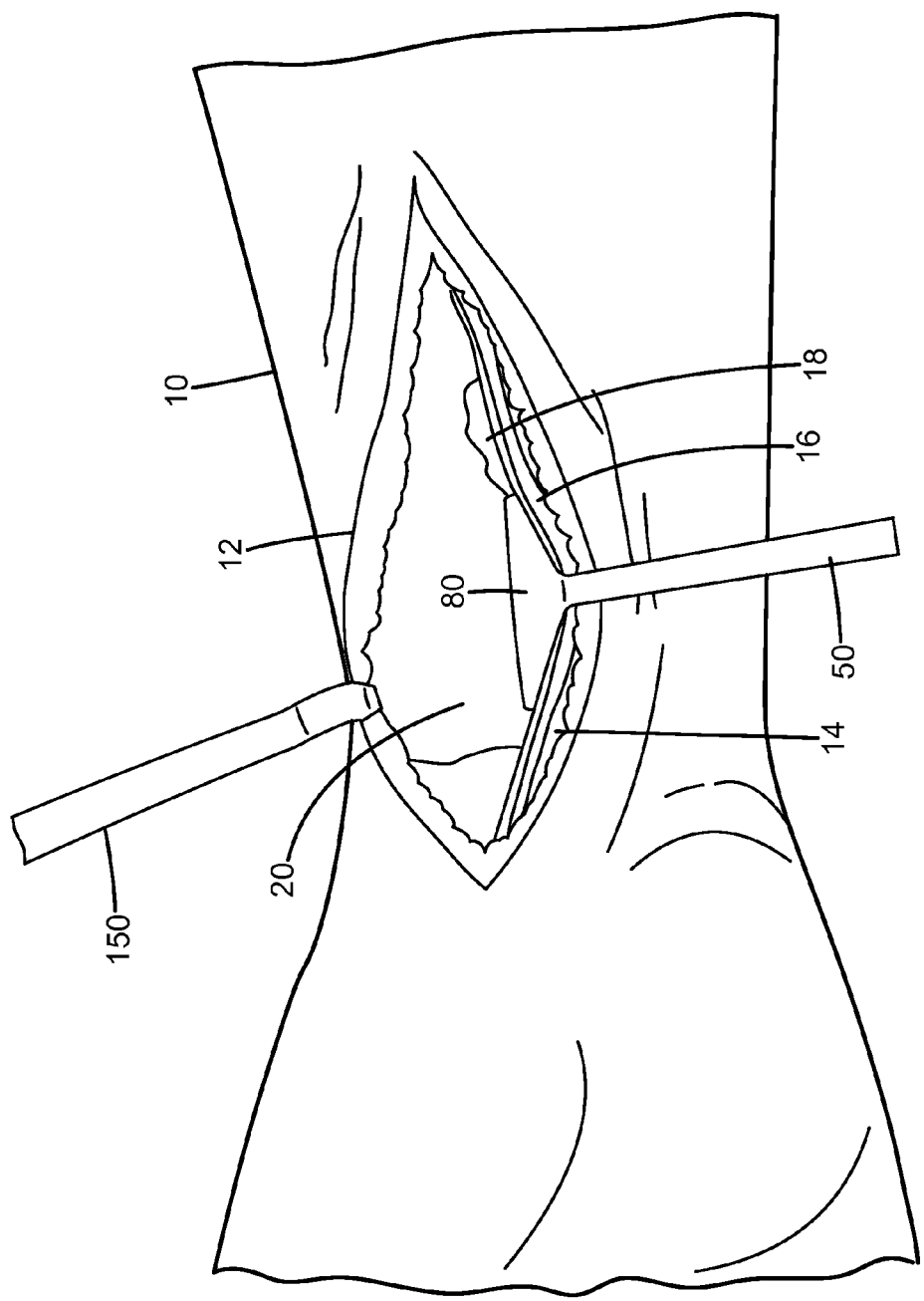
FIG. 5 is a diagrammatic illustration of an exemplary embodiment of a surgical retractor embodying aspects of the invention, in use during a surgical procedure.

The wing or flange portion 80 is rectangular, with rounded corners and edges, and sized to only retract the pronator (which is deep, relative to the skin incision) and to not put pressure on the median nerve (which is above the pronator and more superficial in relation to the skin incision). This is illustrated in FIGS. 5 and 6). Here, the retractor 50 is shown (exclusive of the handle portion being held by a member of the operating team) in place within the field within the incision 12 formed in the patient's wrist 10. The incision has exposed the FCR tendon 14, the median nerve 16, the pronator quadratus muscle 18, and the radius bone 20. The tip of the retractor has been hooked under the bone 20, and is not visible in FIGS. 5 and 6. The wing portion 80 of the retractor has retracted a substantial region of the muscle 18, and the retractor portion above the wing portion has retracted the median nerve, thus providing access to the radius bone 20 for the application of the plate. A second conventional retractor 150 is shown as holding open the outer side of the incision in the skin tissues.

The retractor 50 in this exemplary embodiment is a unitary one-piece structure, fabricated of a stainless steel or other rigid high-strength material, which is preferably inert to the human body. Other suitable materials include titanium and plastic materials.

Although the foregoing has been a description and illustration of specific embodiments of the subject matter, various modifications and changes thereto can be made by persons skilled in the art without departing from the scope and spirit of the invention.

What is claimed is:

1. A method of retracting a patient's pronator quadrator muscle and median nerve during a surgical procedure involving a wrist incision to repair wrist distal radius bone fractures, comprising:
    using a retractor having a hook portion, a handle portion configured for grasping by a surgeon or other medical personnel, a transverse wing portion between the hook portion and the handle portion, and a first intermediate portion between the wing portion and the handle portion, engaging the radius bone with the hook portion of the retractor, and applying pressure to the handle portion to engage and retract the pronator quadrator muscle with the transverse wing portion to provide an open unobstructed field for the surgeon in the wrist incision;
    wherein the transverse wing portion has a width sufficient to retract the pronator muscle away from the field of interest in the incision and a wing portion height in a direction transverse to the width is sufficiently small that the wing portion does not significantly engage the median nerve located superficially with respect to the pronator muscle;
    while continuing to apply pressure to the handle portion, engaging the median nerve with the intermediate portion of the retractor without contacting the nerve with the wing portion and applying a retractor force to the median nerve to retract the median nerve, the intermediate portion have a width smaller than the width of the transverse wing portion so that the retraction force applied to the median nerve is applied over an area smaller than an area of the transverse wing portion, to reduce the possibility of nerve damage.

2. The method of claim 1, wherein the retractor further comprises a second intermediate portion located between the hook portion and the transverse wing portion, and the method further includes:
    contacting the radius bone with the second intermediate portion as pressure is applied to stabilize the retractor on the radius bone, the second intermediate portion having a width smaller than the width of the transverse wing portion.

3. The method of claim 1 wherein the height of the wing portion is about 1.2 cm, and the width of the wing portion is about 2.5 cm.

4. The method of claim 3, wherein the wing portion is positioned above a tip of the hook portion of the retractor by about 1.4 cm.

5. The method of claim 1, wherein the wing portion is disposed at an angular offset relative to the handle portion, wherein the angular offset is in a range between 10 degrees and 40 degrees.

6. The method of claim 1, wherein the handle portion has a width adjacent the first intermediate portion which is smaller than the width of the wing portion.

7. A method of retracting a patient's pronator quadrator muscle and median nerve during a surgical procedure involving a wrist incision to repair wrist distal radius bone fractures, comprising a sequence of the following steps:
    using a retractor having a hook portion at a distal end, a handle portion configured for grasping by a surgeon or other medical personnel, a transverse wing portion between the hook portion and the handle portion, and a first intermediate portion between the wing portion and the handle portion, inserting the distal end of the retractor through the wrist incision and engaging the radius bone with the hook portion of the retractor;
    applying pressure to the handle portion to engage and retract the pronator quadrator muscle with the transverse wing portion to provide an open unobstructed field for the surgeon in the wrist incision while not engaging the median nerve located superficially with respect to the pronator quadratus muscle with the transverse wing portion, the transverse wing portion having a width sufficient to retract the pronator muscle away from the field of interest in the incision and a wing portion height in a direction transverse to the width smaller than the width dimension and sized so that the wing portion does not significantly engage the median nerve located superficially with respect to the pronator muscle;
    while continuing to apply pressure to the handle portion, engaging the median nerve with the intermediate portion of the retractor without contacting the nerve with the wing portion and applying a retractor force to the median nerve to retract the median nerve, the intermediate portion have a width smaller than the width of the transverse wing portion so that the retraction force applied to the median nerve is applied over an area smaller than an area of the transverse wing portion, to reduce the possibility of nerve damage.

\* \* \* \* \*